(12) United States Patent
O'Rear et al.

(10) Patent No.: US 6,225,359 B1
(45) Date of Patent: May 1, 2001

(54) PROCESS FOR CONVERSION OF NATURAL GAS AND ASSOCIATED LIGHT HYDROCARBONS TO SALABLE PRODUCTS

(75) Inventors: Dennis John O'Rear, Petaluma; Charles L. Kibby, Benicia; Russell R. Krug, Novato, all of CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 09/470,328

(22) Filed: Dec. 21, 1999

(51) Int. Cl.⁷ .................... C07C 27/00; C07C 7/20; C07C 6/00; C10G 73/02; C10B 57/02

(52) U.S. Cl. ............... 518/706; 518/702; 518/703; 518/704; 518/706; 208/28; 208/49; 585/1; 585/643; 585/700; 585/708

(58) Field of Search ................... 518/700, 702, 518/703, 704, 706; 208/28, 49; 585/1, 643, 700, 708

(56) References Cited

U.S. PATENT DOCUMENTS

| | | |
|---|---|---|
| 3,484,499 | 12/1969 | Lester et al. ............... 260/673 |
| 3,668,268 | 6/1972 | Mulaskey ............... 260/676 |
| 3,773,845 | 11/1973 | Hughes ............... 260/676 R |
| 3,856,876 | 12/1974 | Burnett ............... 260/676 R |
| 3,864,417 | 2/1975 | Hughes ............... 260/676 R |
| 3,953,537 | 4/1976 | Chloupek et al. ........ 260/676 R |
| 4,676,885 | 6/1987 | Bush ............... 208/49 |

*Primary Examiner*—Johann Richter
*Assistant Examiner*—J. Parsa
(74) *Attorney, Agent, or Firm*—Burns, Doane, Swecker & Mathis LLP (57) ABSTRACT

Salable hydrocarbon products prepared by reacting a light hydrocarbon gaseous stream with a gaseous oxidant to produce carbon oxides and hydrogen, which is contacted in a hydrocarbon synthesis zone to produce a product stream comprising salable hydrocarbon products. That product stream is separated into a gaseous fraction and at least one fraction of salable hydrocarbon products. The light hydrocarbon gaseous stream is formed by separating a light hydrocarbon gaseous feed comprising alkanes into a lighter fraction and a heavier fraction and contacting that heavier fraction in a disproportionation zone to convert a significant portion of the alkanes in the heavier fraction by disproportionation into both higher and lower alkanes, then at least part of the lighter fraction and the lower alkanes form the light hydrocarbon gaseous stream.

16 Claims, 3 Drawing Sheets

PROCESS FOR CONVERSION OF NATURAL GAS AND ASSOCIATED LIGHT HYDROCARBONS TO SALABLE PRODUCTS

The present invention relates to a process for conversion of natural gas and associated light hydrocarbons into salable hydrocarbon products, using molecular redistribution to reduce the amount of gas processed through the most expensive reforming and synthesis sections of the facility and to increase the yield of most valuable products.

BACKGROUND OF THE INVENTION

In a typical process for conversion of natural gas and associated light hydrocarbons into salable hydrocarbon products, methane, a gaseous oxidant, and $C_2$ to $C_6$ hydrocarbons from a gas well are fed to a reforming zone to produce a first product stream comprising carbon oxides (such as carbon monoxide and carbon dioxide), hydrogen, and some water. That first product stream is feed into a hydrocarbon synthesis zone with a hydrocarbon synthesis catalyst at elevated temperature and pressure to produce a second product stream having a wide range of products: from light hydrocarbons to heavy wax. The second product stream is separated in a distillation column into a light hydrocarbon fraction, at least one fraction of salable hydrocarbon products (such as a naphtha stream and a distillate fuels stream), and a waxy fraction. The waxy fraction is hydrotreated to remove heteroatoms and is hydrocracked, then the hydrotreated, hydrocracked waxy fraction is recycled to the distillation column. The light hydrocarbon fraction is recycled to the reforming zone.

A problem with such a process is that it requires that large volumes of light hydrocarbon fraction be fed to and recycled to the reforming zone, which means that both the reforming zone and the hydrocarbon synthesis zone have to be large to accommodate such large volumes of recycle gas. Therefore, it would be advantageous to develop processes that do not require such large volumes of recycle gas. In addition, processing $C_{3+}$ hydrocarbons in the reforming zone can cause coking and metal dusting problems which make operation difficult.

Another problem with such a process is that a mixture of products is made which typically include LPG, naphtha, distillate fuel, and hydrocarbons in the lube base oil range. The hydrocarbons in the lube base oil range and distillate fuel are the most valuable products, but with the existing technology it is not practical to increase the yield of the most valuable products beyond a certain limit. In particular the export of the least valuable LPG product requires the use of pressurized containers for storage and shipment, which represent a significant expense, operational difficulties, and safety hazards. The naphtha from such a process typically has a very low octane value and makes a relatively poor feedstock to a reformer, and is only of moderate value when used as a feed to an ethylene naphtha cracker. While it is desirable to reduce or eliminate the production of LPG and naphtha, with the current process it is not possible to do so. Similarly, the diesel and hydrocarbons in the lube base oil range fractions are the most valuable, but with the current technology the yield of these most valuable fractions cannot be increased beyond a given value.

The disproportionation of saturated hydrocarbons has been described in the patent literature in U.S. Pat. Nos. 3,484,499; 3,668,268; 3,856,876; 3,864,417; and 3,953,537. In the general literature see Hughes, T. R., et. al., Proc. Int. Congr. Catal., 5th (Paper 87) 1972 and Burnett R. L., et. al., Jour. of Cat. 31, pp 55–64, 1973. In the petroleum industry, disproportionation has been proposed for the conversion of refinery gases (see, for example, U.S. Pat. No. 3,773,845) and for the reforming of distillate transportation fuels (see, for example, U.S. Pat. No. 4,676,885).

SUMMARY OF THE INVENTION

The present invention provides processes for conversion of natural gas and associated light hydrocarbons into salable hydrocarbon products, wherein disproportionation of saturated hydrocarbons is used to reduce the amount of light gas recycle needed, and reduce the reactor size needed for the reforming zone and the hydrocarbon synthesis zone.

By "salable hydrocarbon products" we mean any hydrocarbon products having an identifiable market, including but not limited to naphtha, diesel, jet, distillate fuel, hydrocarbons in the lube base oil range, waxes, paraffinic solvents, feedstocks for making detergents, and alcohols.

In one embodiment, the present invention is an improvement on the process for the preparation of salable hydrocarbon products comprising:

(a) reacting a light hydrocarbon gaseous stream with a gaseous oxidant (preferably water, carbon dioxide, oxygen, air, or oxygen-enriched air, or mixtures thereof) in at least one reforming zone containing a reforming catalyst under conditions selected to produce a first product stream comprising carbon oxides (e.g., carbon monoxide and carbon dioxide) and hydrogen;

(b) contacting the first product stream in a hydrocarbon synthesis zone with a hydrocarbon synthesis catalyst under conditions selected to produce a second product stream comprising salable hydrocarbon products; and (c) separating the second product stream into at least a gaseous fraction and at least one fraction of salable hydrocarbon products.

In that improvement, the light hydrocarbon gaseous stream comprised of predominately $C_1$ and $C_2$ alkanes is formed by separating a light hydrocarbon gaseous feed comprising alkanes into a lighter fraction (preferably comprised of predominately $C_1$ and $C_2$ alkanes) and a heavier fraction (preferably comprised of predominately $C_{3+}$ alkanes). At least a portion of this heavier fraction is contacted in a disproportionation zone with a disproportionation catalyst under conditions selected to convert a significant portion of the alkanes in the heavier fraction by disproportionation into both higher alkanes and lower alkanes. At least part of the lighter fraction and at least part of the lower alkanes from the disproportionation zone form the light hydrocarbon gaseous stream. The higher alkanes from the disproportionation zone constitute salable hydrocarbon products.

If the hydrocarbon synthesis zone is a methanol synthesis zone, then methanol is produced. If the hydrocarbon synthesis zone is a Fischer Tropsh zone then the salable hydrocarbon products are likely to be a naphtha fraction and a distillate fuels fraction.

Preferably, if the hydrocarbon synthesis zone is a Fischer Tropsh zone, then the second product stream is separated into at least a gaseous fraction, at least one fraction of salable hydrocarbon products (e.g., a naphtha fraction, a distillate fuels fraction, hydrocarbons in the lube base oil range), and a waxy products fraction. The waxy products fraction being hydrocracked and recycled to the second product stream.

In a second embodiment, the present invention is an improvement on the process for the preparation of salable hydrocarbon products comprising:

(a) reacting a light hydrocarbon gaseous stream (predominately $C_1$ and $C_2$ alkanes) with a gaseous oxidant (preferably water, carbon dioxide, oxygen, air, or oxygen-enriched air, or mixtures thereof) in at least one reforming zone containing a reforming catalyst under conditions selected to produce a first product stream comprising oxides (e.g., carbon monoxide and carbon dioxide) and hydrogen;

(b) contacting the first product stream in a hydrocarbon synthesis zone with a hydrocarbon synthesis catalyst under conditions selected to produce a second product comprising salable hydrocarbon products; and (c) separating the second product stream into at least a gaseous fraction of predominately $C_2$-alkanes, a gaseous fraction of predominately $C_3$–$C_6$ alkanes, at least one fraction of salable hydrocarbon products (preferably a naphtha fraction and a distillate fuels fraction), and a waxy fraction In that improvement, the light hydrocarbon gaseous stream is formed by separating a light hydrocarbon gaseous feed comprising alkanes into a lighter fraction and a heavier fraction, then at least part of the lighter fraction and at least part of the gaseous fraction form the light hydrocarbon gaseous stream. The heavy product fraction (preferably the waxy fraction) and a lighter material (preferably the heavier fraction from the light hydrocarbon gaseous feed) are reacted in a molecular averaging zone with a molecular averaging catalyst under conditions selected to convert a significant portion by molecular averaging into a third product stream comprising salable products, which is preferably recycled to the second product stream.

BRIEF DESCRIPTION OF THE DRAWINGS

In order to assist the understanding of this invention, reference will now be made to the appended drawings. The drawings are exemplary only, and should not be construed as limiting the invention.

DETAILED DESCRIPTION OF THE INVENTION

In its broadest aspect, the present invention involves processes for conversion of natural gas and associated light hydrocarbons into salable hydrocarbon products, wherein molecular redistribution is used to reduce the amount of light gas recycle needed and to reduce the amount of gas processed in the reformer. In one embodiment, the molecular redistribution is a disproportionation, where some of the alkanes are converted into higher alkanes and lower alkanes. The higher alkanes have higher molecular weights than the original material and the lower alkanes have lower molecular weights than the original material. In the second embodiment, the molecular redistribution is a molecular averaging, where heavier alkanes and lighter alkanes are converted into materials having molecular weights between the two original materials, thus increasing the production of the desired salable product.

The Feed

In both processes of the present invention, the initial feed is a light hydrocarbon gaseous feed of alkanes (predominately $C_1$ to $C_6$ alkanes), such as might come from a gas well. This light hydrocarbon gaseous feed should be treated to remove sulfur, oxygen, nitrogen, and other heteroatoms. Treatments for removal of such heteroatoms are well known in the art.

In a conventional process for conversion of natural gas and associated light hydrocarbons into salable hydrocarbon products, the light hydrocarbon gaseous feed would be fed to a reforming zone to produce a product stream comprising oxides (e.g., carbon monoxide and carbon dioxide), hydrogen, and some water.

In the present invention, this light hydrocarbon gaseous feed is separated into a lighter fraction and a heavier fraction. Preferably, the lighter fraction is predominately $C_1$ and $C_2$ alkanes, although there may be some heavier alkanes present. Preferably, the heavier is predominately $C_3$ and higher alkanes, although there may be some lighter alkanes present. Only the lighter fraction is sent to the reforming zone to produce carbon oxides and hydrogen, with some water.

In one embodiment, the heavier fraction (predominately $C_3$ and higher alkanes) is sent to a disproportionation zone, where a significant portion of it is converted into lower alkanes (predominately $C_1$ and $C_2$ alkanes) and salable product. In another embodiment, it is sent to a molecular averaging zone, where it is reacted with a hydrotreated waxy fraction to produce salable products. In none of the embodiments does it go to the reforming zone, therefore the reforming zone and the hydrocarbon synthesis zone can be much smaller.

The Disproportionation Zone

In one embodiment, $C_3$ and higher alkanes are contacted in a disproportionation zone with a disproportionation catalyst under conditions selected to convert a significant portion of those alkanes by disproportionation into both higher alkanes (predominately salable product) and lower alkanes (predominately $C_1$–$C_2$ alkanes). The higher alkanes are used as a salable hydrocarbon products stream, or are blended into another salable hydrocarbon products stream, such as a naphtha stream. The lower alkanes are used as part of the light hydrocarbon gaseous stream going to the reforming zones.

The term "disproportionation" is used in this disclosure to mean the conversion of alkanes or olefins to new hydrocarbons of both lower and higher molecular weight. For example, the alkane, butane, may be converted by disproportionation according to the following reaction:

$$2C_4H_{10} \leftrightarrow C_3H_8 + C_5H_{12}$$

Various methods have been described in the literature, which are suitable for the removal of sulfur from the well gas. For example, treatment with amines may be used to remove hydrogen sulfide from the well gas. Organic sulfur compounds, such as mercaptans, may be removed by treatment with caustic or by hydrogenation processes such as hydrotreating. However, in such an instance a local source of hydrogen would be required for the hydrotreating step. Specific commercial processes are available for the removal of sulfur compounds from well gases and are well known to those skilled in the art.

In addition, the presence of ammonia and moisture in the feed to the reactor have been reported to have a deleterious effect on some disproportionation catalysts. Commercial processes that may be used to remove these contaminants from the feed to the disproportionation reactor are well known to those skilled in the art. The presence of excess olefins and hydrogen in the disproportionation zone are also known to effect the equilibrium of the disproportionation reaction and to deactivate the catalyst. Saturated cyclic hydrocarbons and partially saturated cyclic hydrocarbons can produce hydrogen and limit the extent of conversion. These species should be substantially excluded from the feed. Since the composition of the well gas will vary with location, some routine experimentation will be necessary to identify the contaminants that are present and identify the optimal processing scheme and catalyst to use in carrying out the invention.

Various catalysts are known to catalyze the disproportionation reaction. The catalyst mass used to carry out the present invention must have both dehydrogenation/hydrogenation activity and disproportionation activity. The dehydrogenation activity is believed to be necessary to convert the alkanes in the feed to olefins, which are believed to be the actual species that undergo disproportionation. Following disproportionation, the olefin is converted back into an alkane. It is theorized that the dehydrogenation/hydrogenation activity of the catalyst also contributes to rehydrogenation of the olefin to an alkane. While it is not intended that the present invention be limited to any particular mechanism, it may be helpful in explaining the choice of catalysts to further discuss the sequence of chemical reactions which are believed to be responsible for disproportionation of the alkanes. As an example, the general sequence of reactions for butane is believed to be:

$$2C_4H_{10} \leftrightarrow 2C_4H_8 + 2H_2 \leftrightarrow C_3H_6 + C_5H_{10} + 2H_2 \leftrightarrow C_3H_8 + C_5H_{12}$$

The catalyst mass for use in the disproportionation zone will be dual function and may have the two functions on the same catalyst particle or may consist of different catalysts having separate dehydrogenation/hydrogenation and disproportionation components within the catalyst mass. The dehydrogenation/hydrogenation function within the catalyst mass usually will include a Group VIII metal from the Periodic Table of the Elements which includes iron, cobalt, nickel, palladium, platinum, rhodium, ruthenium, osmium, and iridium. Platinum and palladium or the compounds thereof are preferred for inclusion in the dehydrogenation/hydrogenation component, with platinum or a compound thereof being especially preferred. As noted previously, when referring to a particular metal in this disclosure as being useful in the present invention, the metal may be present as elemental metal or as a compound of the metal. As discussed above, reference to a particular metal in this disclosure is not intended to limit the invention to any particular form of the metal unless the specific name of the compound is given, as in the examples in which specific compounds are named as being used in the preparations.

In the event the catalyst deactivates with the time-on-stream, specific processes that are well known to those skilled in art are available for the regeneration of the catalysts.

Usually the disproportionation component of the catalyst mass will include one or more of a metal or the compound of a metal from Group VIB or Group VIIB of the Periodic Table of the Elements, which include chromium, manganese, molybdenum, rhenium, and tungsten. Preferred for inclusion in the disproportionation component are molybdenum, rhenium, tungsten, and the compounds thereof. Particularly preferred for use in the disproportionation component is tungsten or a compound thereof. As discussed, the metals described, above, may be present as elemental metals or as compounds of the metals, such as, for example, as an oxide of the metal. It is also understood that the metals may be present on the catalyst component either alone or in combination with other metals.

In most cases the metals in the catalyst mass will be supported on a refractory material. Refractory materials suitable for use as a support for the metals include conventional refractory materials used in the manufacture of catalysts for use in the refining industry. Such materials include, but are not necessarily limited to, alumina, zirconia, silica, boria, magnesia, titania and other refractory oxide material or mixtures of two or more of any of the materials. The support may be a naturally occurring material, such as clay, or synthetic materials, such as silica-alumina and borosilicates. Molecular sieves, such as zeolites, also have been used as supports for the metals used in carrying out the dual functions of the catalyst mass. See, for example, U.S. Pat. No. 3,668,268. Mesoporous materials such MCM-41 and MCM-48, such as described in Kresge, C. T., et. al., Nature (Vol. 359) pp. 710–712, 1992, may also be used as a refractory support. Other known refractory supports, such as carbon, may also serve as a support for the active form of he metals in certain embodiments of the present invention. The support is preferably non-acidic, i.e. having few or no free acid sites on the molecule. Free acid sites on the support may be neutralized by means of alkali metal salts, such as those of lithium. Alumina, particularly alumina on which the acid sites have been neutralized by a alkali salt, such as lithium nitrate, is usually preferred as a support for the dehydrogenation/hydrogenation component, and silica is usually preferred as the support for the disproportionation component.

The amount of active metal present on the support may vary, but it must be at least a catalytically active amount, i.e., a sufficient amount to catalyze the desired reaction. In the case of the dehydrogenation/hydrogenation component the active metal content will usually fall within the range from about 0.01 weight percent to about 50 weight percent on an elemental basis, with the range of from about 0.1 weight percent to about 20 weight percent being preferred. For the disproportionation component, the active metals content will usually fall within the range of from about 0.01 weight percent to about 50 weight percent on an elemental basis, with the range of from about 0.1 weight percent to about 15 weight percent being preferred.

A typical disproportionation catalyst for use in the present invention which includes a platinum component and a tungsten component is described in U.S. Pat. No. 3,856,876, the entire disclosure of which is herein incorporated by reference. In one embodiment of the present invention a catalyst is employed which comprises a mixture of platinum-on-alumina and tungsten-on-silica, wherein the volumetric ratio of the platinum component to the tungsten component is greater than 1:50 and less than 50:1. Preferably the volumetric ratio of the platinum component to the tungsten component in this particular embodiment is between 1:10 and 10:1. The percent of surface of the metals should be maximized with at least 10% of the surface metal atoms exposed to the reactant.

Both the dehydrogenation/hydrogenation component and the disproportionation component may be present within the catalyst mass on the same support particle as, for example, a catalyst in which the dehydrogenation/hydrogenation component is dispersed on an unsupported disproportionation component such as tungsten oxide. In another embodiment of the invention, the catalyst components may be separated on different particles. When the dehydrogenation/hydrogenation component and the disproportionation component are on separate particles, it is preferred that the two components be in close proximity to one another, as for example, in a physical mixture of the particles containing the two components. However, in other embodiments of the invention, the components may be physically separated from one another, as for example, in a process in which separate dehydrogenation/hydrogenation and disproportionation zones are present in the reactor. In a reactor having a layered fixed catalyst bed, the two components may, in such an embodiment, be separated in different layers within the bed. In some applications it may even be advantageous to have separate reactors for carrying out the dehydrogenation and disproportionation steps. However, in processing schemes where the dehydrogenation of the alkanes to olefins occurs separately from the disproportionation reaction of the olefins, it may be necessary to include an additional hydrogenation step in the process, since the rehydrogenation of the olefins must take place after the disproportionation step.

The process conditions selected for carrying out the present invention will depend upon the disproportionation catalyst used. In general, the temperature in the reaction zone will be within the range of from about 400° F. (200° C.) to about 1,000° F. (540° C.) with temperatures in the range of from about 500° F. (260° C.) to about 850° F. (455° C.) usually being preferred. In general the conversion of the alkanes by disproportionation increases with an increase in pressure. Therefore, the selection of the optimal pressure for carrying out the process will usually be at the highest practical pressure under the circumstances. Accordingly, the pressure in the reaction zone should be maintained above 100 psig, and preferably the pressure should be maintained above 500 psig. The maximum practical pressure for the practice of the invention is about 5000 psig. More typically, the practical operating pressure will below about 3000 psig. The feedstock to the disproportionation reactor should contain a minimum of olefins, and saturated cyclic hydrocarbons, and, preferably, should contain no added hydrogen.

Saturated cyclic hydrocarbons and partially saturated cyclic hydrocarbons (cycloalkanes fused aromatic-cycloalkanes and alkyl-derivatives) in the feed can react under disproportionation conditions to form aromatics and hydrogen. The hydrogen acts to limit the conversion. Fully aromatic cyclic hydrocarbons do not react to form hydrogen and these species can be tolerated in the feed. Saturated cyclic hydrocarbons should be substantially excluded from the feed. Separation of the desired paraffins from the undesired cyclic hydrocarbons can be done by adsorption with molecular sieves, extraction with urea, and deoiling. These methods are well known in the industry. Separation with urea is described by Hepp, Box and Ray in Ind. Eng. Chem., 45: 112 (1953).

Platinum/tungsten catalysts are particularly preferred for carrying out the present invention because the disproportionation reaction will proceed under relatively mild conditions. When using the platinum/tungsten catalysts, the temperature should be maintained within the range of from about 400° F. (200° C.) to about 120° F. (650° C.), with temperatures above about 500° F. (260° C.) and below about 1000° F. (540° C.) being particularly desirable.

One skilled in the art will recognize that the reactions that occur in the disproportionation zone are equilibrium reactions and, as such, it is desirable to reduce the concentration of the desired products in the disproportionation zone to as low a concentration as possible to favor the reactions in the desired direction. Therefore, it is desirable to remove as much of the $C_5$ plus hydrocarbons from the well gas prior to its introduction into the disproportionation zone. In addition, it is preferred that the process be carried under conditions selected to minimize the amount of methane produced in the disproportionation zone. As such, some routine experimentation may be necessary to find the optimal conditions for conducting the process.

The Molecular-averaging Zone

In another embodiment, a heavier process stream (such as the waxy products fraction) and a lighter process stream (such as the $C_{3+}$ alkane fraction, which is predominately $C_3$ to $C_6$) are reacted in a molecular averaging zone with a disproportionation catalyst under conditions selected to convert them by molecular averaging into a product stream comprising salable products.

The lighter process stream that is reacted with the heavier process stream is lighter than the heavier process stream. Preferably, that lighter process stream is the heavier fraction separated from the light hydrocarbon gaseous fraction. This heavier fraction preferably consists of predominately $C_3$–$C_6$ alkanes, as compared to the $C_1$–$C_2$ alkanes of the lighter fraction.

Optionally, the lighter process stream is isomerized prior to molecular averaging, so that the product from the molecular averaging has small branches, thus improving its fluid properties at low temperatures. Isomerization processes are generally carried out at a temperature between 200° F. and 700° F., preferably 300° F. to 550° F., with a liquid hourly space velocity between 0.1 and 2, preferably between 0.25 and 0.50 employing hydrogen such that the hydrogen to hydrocarbon mole ratio is between 1:1 and 5:1. Catalysts useful for isomerization are generally bifunctional catalysts comprising a hydrogenation component, (preferably selected from the Group VIII metals of the Periodic Table of the Elements, and more preferably selected from the group consisting of nickel, platinum, palladium and mixtures thereof) and an acid component. Examples of an acid component useful in the preferred isomerization catalyst include a crystalline zeolite, a halogenated alumina component, or a silica-alumina component. Such paraffin isomerization catalysts are well known in the art for use in isomerizing $C_4$–$C_{10}$ paraffins.

While the heavier fraction separated from the light hydrocarbon gaseous fraction is preferred, other lighter process streams can be used to react with the heavier process stream. For instance, the lighter process stream can be also be the gaseous fraction of predominately $C_3$–$C_6$ alkanes or at least one of the fractions of salable hydrocarbon products from the separator following hydrocarbon synthesis, or mixture thereof.

The heavier process stream that is reacted with the lighter process stream is heavier than the lighter process stream. Examples of the heavier process stream include the waxy products fraction and other salable products, or blends thereof.

Some of the combinations include:

LPG-range hydrocarbons averaged with 1000° F.+ wax to make naphtha, distillate fuels and paraffinic solvents, feedstocks for detergents and alcohols, and hydrocarbons in the lube base oil range.

Naphtha averaged with 1000° F.+ wax to make distillate fuels, paraffinic solvents, feedstocks for detergents and alcohols, and hydrocarbons in the lube base oil range.

Distillate fuel averaged with 1000° F.+ wax to make hydrocarbons in the lube base oil range.

LPG+Naphtha averaged with 1000° F.+ to make distillate fuels, paraffinic solvents, feedstocks for detergents and alcohols, and wax.

Naphtha+distillate fuels averaged with 1000° F.+ wax to make hydrocarbons in the lube base oil range.

LPG+Naphtha+distillate fuels averaged with 1000° F.+ wax to make hydrocarbons in the lube base oil range.

LPG averaged with 700° F.+ full range wax to make naphtha and distillate fuels, paraffinic solvents, and feedstocks for detergents and alcohols.

LPG and naphtha averaged with 700° F.+ full range wax to make distillate fuels, paraffinic solvents, and feedstocks for detergents and alcohols.

Both the heavier process and the lighter process stream should be free of oxygen and other impurities, such as sulfur, nitrogen, olefins, saturated cyclic hydrocarbons, partially saturated cyclic hydrocarbons, catalyst fines, additional hydrogen etc.

The disproportionation reaction described above is reversible, which means that the reaction proceeds to an equilibrium limit. Therefore, if the feed to the disproportionation zone has two streams of alkanes at different molecular weights then equilibrium will drive the reaction to produce product having a molecular weight between that of the two streams. Such a reaction is called molecular averaging, and a zone where it occurs is called a molecular averaging zone.

In the present invention, molecular averaging is used to from salable products from two streams, one (the heavier process stream) having a higher molecular weight than the final desired salable product and the other (the lighter process stream) having a lower molecular weight than the final desired salable product.

Any type of typical catalytic reactor can be used, but if this process is used to convert heavy waxes (1000° F.+) into hydrocarbons in the lube base oil range, the preferred reactor is a catalytic distillation reactor.

The Reforming Zone(s)

In the reforming zone (or zones), a light hydrocarbon gaseous stream is reacted with a gaseous oxidant in the presence of a reforming catalyst to produce a product stream comprising carbon oxides and hydrogen, and possibly water.

In a conventional process, the light hydrocarbon gaseous stream comprises $C_1$ to $C_6$ hydrocarbons from a gas well, and a large volume of recycled $C_1$ to $C_6$ hydrocarbons from the distillation column. In the present invention, the light hydrocarbon gaseous stream comprises predominately $C_1$ and $C_2$ alkanes.

In the present invention, the light hydrocarbon gaseous stream is made up of either the lighter fraction of the light hydrocarbon gaseous feed alone or in combination with light alkanes from the disproportionation zone. If light alkanes from the disproportionation zone are used, they can be blended with the lighter fraction of the light hydrocarbon gaseous feed or they can be fed into the reforming zone as separate light hydrocarbon gaseous streams. Preferably, the gaseous oxidant is water, carbon dioxide, oxygen, air, or oxygen-enriched air, or a mixture thereof.

Reforming is well known in the art, and includes a variety of technologies including steam reforming, partial oxidation, dry reforming, series reforming, convective reforming, and autothermal reforming. All have in common the production of syngas from methane and an oxidant (steam, oxygen, carbon dioxide, air, enriched air or combinations). The effluent typically contains some carbon dioxide and steam in addition to syngas. Series reforming, convective reforming and autothermal reforming incorporate more than one syngas forming reaction in order to better utilize the heat of reaction. These processes for producing synthesis gas or syngas from $C_1$–$C_3$ alkanes are well known to the art. Steam reformation is typically effected by contacting C1–C3 alkanes with steam, preferably in the present of a reforming catalyst, at a temperature in the range of about 1300° F. (705° C.) to about 1675° F. (913° C.) and pressures from about 10 psia (0.7 bars) to about 500 psia (34 bars).

The reforming can be operated in two stages with the first called a pre-reformer. A pre-reformer is often used when the gas feed contains hydrocarbons other than methane ($C_{2+}$). Without a pre-reformer, the $C_{2+}$ hydrocarbons can cause operational problems due to coking and metal dusting. As the hydrocarbons in the feed to the reforming section become heavier, the need for a pre-reformer is greater. Thus use of molecular redistribution to minimize the content of $C_{3+}$ feed in the reformer can reduce the need for the additional pre-reformer, and in some cases eliminate it.

Suitable reforming catalysts which can be used include, for example, nickel, palladium, nickel-palladium alloys, and the like. Additional information regarding steam reforming $C_1$–$C_3$ alkanes, e.g., methane, to syngas can be found in U.S. Pat. No. 5,324,335 hereby incorporated by reference in its entirety. The partial oxidation of $C_1$–$C_3$ alkanes to syngas is also conducted at high temperature and while the partial oxidation may be conducted without a catalyst it is more effectively conducted in the presence of a catalyst. In general Group VIII metals can be used as the catalyst typically supported on a mineral oxide or synthetic support, e.g., alumina. Typically, the partial oxidation is conducted at temperatures in about the range of 1500° F. (815° C.) to about 2000° F. (1093° C.) pressures in about the range from atmospheric to 3000 psia (1 to 20.4 bars). Space velocities can vary over a very wide range and typical range of 100 to 100,000 $hr^{-1}$ and even higher depending on the particular catalyst used and the type of reactor. A discussion of nickel silica alumina and nickel/magnesium oxide and cobalt/magnesium oxide and other oxidation catalysts may be found in A. Santos et al., Oxidation of Methane to Synthesis Gas in Fluidized Bed Reactor using MgO-Based Catalysts, Journal of Catalysis, Vol. 158 (1996) pp. 81–91 hereby incorporated by reference in its entirety. The partial oxidation may also be conducted using a peroskite catalyst partial oxidation process such as described in U.S. Pat. No. 5,149,516 hereby incorporated by reference in its entirety. Peroskites are materials having essentially the same crystal structure as the mineral peroskite (Ca Ti O3) without limitation as to the elemental constituents thereof. Such materials can be represented by the formula $XYO_3$ wherein X and Y can be variety of elements. For example, X can be La, Ca, Sr, Ba, Na, K, Ag, Cd and mixtures thereof and Y can be Ta, Co, Ti, Ga, Nb, Fe, Ni, Mn, Gr, V, Th, Pb, Sn, Mo, Zn and mixtures thereof. Partial oxidation reactions using a peroskite catalyst are typically conducted at temperatures in the range of about from 600 to 900° C., pressures of about from 0.1 to 100 bar and gas hourly space velocities of from 100 to 300,000 hr$^{-1}$. (These space velocities are determined using a gas volume based on NTP conditions, i.e. room temperature (about 25° C.) and one atmosphere of pressure.) The mol ratio of lower alkane can vary from 1:1 to 100:1 moles of alkane to oxygen.

Regardless of the system used to produce syngas it is desirable to remove any sulfur compounds, e.g., hydrogen sulfide and mercaptans, contained in the $C_1$–$C_3$ alkane feed. This can be effected by passing the $C_1$–$C_3$ alkanes gas through a packed bed sulfur scrubber containing zinc oxide bed or another slightly basic packing material. If the amount of $C_1$–$C_3$ alkanes exceeds the capacity of the synthesis gas unit the surplus $C_1$–$C_3$ alkanes can be used to provide energy throughout the facility. For example, excess $C_1$–$C_3$ alkanes may be burned in a steam boiler to provide the steam used in the thermal cracking step of the present process.

The Hydrocarbon Synthesis Zone

The product stream from the reforming zone is passed to a hydrocarbon synthesis zone, where it is contacted with a hydrocarbon synthesis catalyst under conditions selected to produce a product stream comprising at least one salable hydrocarbon product.

In one embodiment, the hydrocarbon synthesis zone is a methanol synthesis zone and the salable hydrocarbon product is methanol. Such methanol synthesis has been known since the mid-1920s. Modern industrial-scale methanol production is based almost exclusively on synthesis from pressurized mixtures of hydrogen and carbon oxide gases in the presence of metallic heterogeneous catalysts, such as highly active, durable copper-zinc oxide catalysts. Typical catalysts would include Zn—Cr, or Cu—Zn or newer materials Ni organometallics (including Ni carbonyl) in the presence of base. Process conditions include a temperature of between 1000 and 400° C., preferably between 100° and 300° C., a pressure less than 50 atmospheres, and a hydrogen to carbon monoxide ratio less than 20, preferably less than 10.

In another embodiment, the hydrocarbon synthesis zone is a Fischer Tropsch zone and there is a wide range of products: from light hydrocarbons to heavy wax. The syngas product is converted to liquid hydrocarbons by contact with a Fischer-Tropsch catalyst under reactive conditions. Depending on the quality of the syngas it may be desirable to purify the syngas prior to the Fischer-Tropsch reactor to remove carbon dioxide produced during the syngas reaction and any sulfur compounds, if they have not already been removed. This can be accomplished by contacting the syngas with a mildly alkaline solution (e.g., aqueous potassium carbonate) in a packed column. In general Fischer-Tropsch catalysts contain a Group VIII transition metal on a metal oxide support. The catalyst may also contain a noble metal promoter(s) and/or crystalline molecular sieves. Pragmatically, the two transition metals which are most commonly used in commercial Fischer-Tropsch processes are cobalt or iron. Ruthenium is also an effective Fischer-Tropsch catalyst but is more expensive than cobalt or iron. Where a noble metal is used, platinum and palladium are generally preferred. Suitable metal oxide supports or matrices which can be used include alumina, titania, silica, magnesium oxide, silica-alumina, and the like, and mixtures thereof.

Although, Fischer-Tropsch processes produce a hydrocarbon product having a wide range of molecular sizes the selectivity of the process toward a given molecular size range as the primary product can be controlled to some extent by the particular catalyst used. In the present process, it is preferred to produce $C_{20}$–$C_{50}$ paraffins as the primary product, and therefore, it is preferred to use a cobalt catalyst although iron catalysts may also be used. One suitable catalyst which can be used is described in U.S. Pat. No. 4,579,986 as satisfying the relationship.

$$(3+4R)>L/S>(0.3+0.4R),$$

wherein

L=the total quantity of cobalt present on the catalyst, expressed as mg Co/ml catalyst, S=the surface area of the catalyst, expressed as m2/ml catalyst, and R=the weight ratio of the quantity of cobalt deposited on the catalyst by kneading to the total quantity of cobalt present on the catalyst.

Preferably, the catalyst contains about 3–60 ppw cobalt, 0.1–100 ppw of at least one of zirconium, titanium or chromium per 100 ppw of silica, alumina, or silica-alumina and mixtures thereof. Typically, the synthesis gas will contain hydrogen, carbon monoxide and carbon dioxide in a relative mole ratio of about from 0.25 to 2 moles of carbon monoxide and 0.01 to 0.05 moles of carbon dioxide per mole of hydrogen. In the present process we prefer to use a mole ratio of carbon monoxide to hydrogen of about 0.4 to 1, more preferably 0.5 to 0.7 moles of carbon monoxide per mole of hydrogen with only minimal amounts of carbon dioxide; preferably less than 0.5 mole percent carbon dioxide.

In the present process the Fischer-Tropsch reaction is typically conducted at temperatures of about from 300 to 700° F. (149 to 371° C.) preferably about from 4000 to 550° F. (204° to 228° C.); pressures of about from 10 to 500 psia, (0.7 to 34 bars) preferably 30 to 300 psia, (2 to 21 bars) and catalyst space velocities of about from 100 to 10,000 cc/g/hr., preferably 300 to 3,000 cc/g/hr. The reaction can be conducted in a variety of reactors for example, fixed bed reactors containing one or more catalyst beds, slurry reactors, fluidized bed reactors, or a combination of different type reactors. The Fischer-Tropsch reaction product can be separated into the desired product fractions, e.g., a gasoline fraction (B.P. about 68–450° F./20–232° C.) a middle distillate fraction (B.P. about 450–650° F./232–343° C.) a wax fraction (B.P. about 650–1100° F./539° C.) primarily containing $C_{20}$ to $C_{50}$ normal paraffins with a small amount of branched paraffins and a heavy fraction (B.P. above about 1100° F.) and tail gases. With the exception of the wax fraction, the other fractions are largely a matter of choice depending on the products desired; for example, a single liquid fuel fraction may be taken off comprising both gasoline and middle distillate may be taken off or multiple fuel cuts as well as heavy cuts may be taken. In some cases, for example, where a bubble slurry reactor is used, both liquid and gaseous product streams may be taken off. The gaseous stream will contain tail gases and may also contain gasoline fuel fraction. The gasoline fraction can be recovered using vapor/liquid separators. The tail gas primarily containing hydrogen and $C_1$ to $C_4$ paraffins can be used as fuel gas or can be treated to remove carbon dioxide and used as a hydrogen or alkane recycle stream.

In a preferred embodiment, the Fischer-Tropsch reaction is conducted in a bubble column slurry reactor. In this type of reactor synthesis gas is bubbled through a slurry comprising catalyst particles in a suspending liquid. Typically the catalyst has a particle size of about from 10–110 microns, preferably about from 20–80 microns, more preferably about from 25–65 micron and a density of about from 0.25 to 0.9 g/cc preferably about from 0.3–0.75 g/cc. The catalyst typically comprises one of the aforementioned catalytic metals, preferably cobalt on one of the aforementioned catalyst supports. Preferably the catalyst comprises about 10 to 14 wt. % cobalt on a low density fluid support, for example alumina, silica and the like having a density within the ranges set forth above for the catalyst. Since, the catalyst metal may be present in the catalyst as oxides the catalyst is typically reduced with hydrogen prior to contact with the slurry liquid. The starting slurry liquid is typically a heavy hydrocarbon having a viscosity high enough to keep the catalyst particles suspended, typically a viscosity between 4–100 centistokes at 100° C.) and a low enough volatility to avoid vaporization during operation, typically an initial boiling point range of about from 350 to 550° C. The slurry liquid is preferably essentially free of contaminants such as sulfur, phosphorous or chlorine compounds. Thus initially, it may be desirable to use a synthetic hydrocarbon fluid such as a synthetic olefin oligomer as the slurry fluid. Ultimately, a paraffin fraction of the product having the desired viscosity and volatility is typically recycled as the slurry liquid. The slurry typically has a catalyst concentration of about 240 wt. % catalyst, preferably 5–20 wt. % and more preferably 7–15 wt. % catalyst based on the total weight of the catalyst, i.e. metal plus support. The syngas feed typically has hydrogen to carbon monoxide mole ratio of about from 0.5 to 4 moles of hydrogen per mole of carbon monoxide preferably about from 1 to 2.5 and more preferably about 1.5 to 2.

The bubble slurry reactor is typically operated at temperatures within the range of 150–300° C., preferably 185 to 265° C. and more preferably 210–230° C. and pressures within the range of 1 to 70 bar, preferably 6–35 bar and most preferably 10 to 30 bar (1 bar=14.5 psia). Typical synthesis gas linear velocity ranges in the reactor from about 2 to 40 cm per sec. preferably 6 to 10 cm per sec. Additional details regarding bubble column slurry reactors can, for example, be found in Y. T. Shah et al., Design Parameters Estimations for Bubble Column Reactors, AIChE Journal, 28 No. 3 pp. 353–379 (May 1982); Ramachandran et al., Bubble Column Slurry Reactor, Three-Phase Catalytic Reactors Chapter 10, pp. 308–332 Gordon and Broch Science Publishers (1983); Deckwer et al., Modeling the Fischer-Tropsch Synthesis in the Slurry Phase, Ind. Eng. Chem. Process Des. Dev. v 21, No. 2, pp. 231–241 (1982); Kölbel et al., The Fischer-Tropsch Synthesis in the Liquid Phase, Catal. Rev.-Sci. Eng., v. 21(n), pp. 225–274 (1980) and U.S. Pat. No. 5,348,982, all of which are hereby incorporated by reference in their entirety.

The gaseous reaction product from the Fischer-Tropsch bubble slurry reactor comprises hydrocarbons boiling below about 650° F. (e.g., tail gases through middle distillates). The liquid reaction product is recovered as or with the slurry and comprises hydrocarbons boiling above about 650° F., e.g., vacuum gas oil through heavy paraffins. The minus 650° F. product can be separated into a tail gas fraction and a condensate fraction, i.e., about $C_5$ to $C_{20}$ normal paraffins and higher boiling hydrocarbons, using a high pressure and/or lower temperature vapor-liquid separator or low pressure separators or a combination of separators. The tail gas fraction may be used as described above. The condensate fraction can be fractionated into the desired product fraction; e.g., gasoline, light middle distillate or more preferably is upgraded by hydrocracking. The F-T fraction boiling above about 650° F., after removal of the particulate catalyst, is typically separated into a wax fraction boiling in the range of about 650° F.–1100° F. primarily about containing $C_{20}$ to $C_{50}$ linear paraffins with relatively small amounts of higher boiling branched paraffins, one or more liquid fuel fractions boiling below about 650° F. and one or more fractions boiling above about 1100° F. Typically, the separation is effected by fractional distillation. A portion of the liquid reaction product is preferably recycled to provide slurry liquid.

Alternatively, if the Fischer-Tropsch reaction is designed to produce a single process stream, for example, by using fixed bed reactor, then the entire product stream may be fractionated generally after first removing hydrogen and preferably other tail gases as well. This can be done by passing the product stream through one or more vapor-liquid separators prior to fractionation Although the invention is described herein in terms of a Fischer-Tropsch reaction product or a Fischer-Tropsch process the invention also applies to the various modifications of the literal Fischer-Tropsch process by which hydrogen (or water) and carbon monoxide (or carbon dioxide) are converted to hydrocarbons (e.g. paraffins, ethers etc.) and to the products of such processes. Thus the term Fischer-Tropsch type product or process is intended to apply to Fischer-Tropsch processes and products and the various modifications thereof and the products thereof. For example, the term is intended to apply to the Kolbel-Engelhardt process typically described by the reactions

The Separation of Product

If the hydrocarbon synthesis is Fischer Tropsch, then the product from the hydrocarbon synthesis zone is separated into at least one gaseous fraction, at least one fraction of salable hydrocarbon products, and possibly a waxy products fraction. Preferably, there are at least two fractions of salable hydrocarbon products: a naphtha fraction and a distillate fuels fraction. In addition, hydrocarbons in the lube base oil range can also be produced. This separation can be done by conventional distillation.

The gaseous fraction can be recycled to the disproportionation zone or to the first separator. In either case, olefins, saturated cyclic hydrocarbons, partially saturated cyclic hydrocarbons, and oxygenated compounds (which would include alcohols, acids, aldehydes, ketones, etc.) need to be removed from the gaseous fraction prior to recycle.

The Hydrotreating Zone

If there is a waxy products fraction, it is preferably treated (e.g., hydrotreated in a hydrotreating zone) to remove oxygen and other impurities to form a treated waxy fraction. Such hydrotreating zones are well known in the industry. The catalysts and procedures used in the hydrotreating zone may also be used to partially hydrocrack the feed. If partial hydrocracking is conduced in the hydrotreating zone, the conversion to lower boiling range fractions should be below 75%, and preferably below 50%. If hydrocracking is done as part of this process, the catalysts described in the Hydrocracking zone may be used.

Other treatments useful for removing oxygen and other impurities include, but are not limited to, adsorption and extraction. Saturated cyclic hydrocarbons and partially saturated cyclic hydrocarbons may be separated from the desired feedstock paraffins by using adsorption with molecular sieves, or by deoiling, or by complexing with urea.

The Hydrocracking Zone

The waxy products fraction can be hydrocracked and then the hydrocracked product can be recycled to the product stream coming from the hydrocarbon synthesis zone.

Hydrocracking can be effected by contacting the particular fraction or combination of fractions, with hydrogen in the presence of a suitable hydrocracking catalyst at temperatures in the range of about from 600 to 900° F. (316 to 482° C.) preferably 650 to 850° F. (343 to 454° C.) and pressures in the range about from 200 to 4000 psia (13–272 atm) preferably 500 to 3000 psia (34–204 atm) using space velocities based on the hydrocarbon feedstock of about 0.1 to 10 $hr^{-1}$ preferably 0.25 to 5 $hr^{-1}$. Generally, more severe conditions within these ranges will be used with higher boiling feedstocks and depending on whether gasoline, middle distillate or lubricating oil is desired as the primary economic product. The hydrocracking step reduces the size of the hydrocarbon molecules, hydrogenates olefin bonds, hydrogenates aromatics, and removes traces of heteroatoms resulting in an improvement in fuel or base oil product quality.

As is well known the hydrocracking catalysts contain a hydrogenation component and a cracking component. The hydrogenation component is typically a metal or combination of metals selected from Group VIII noble and non-noble metals and Group VIB metals. The noble metals, particularly platinum or palladium, are generally more active but are expensive. Non-noble metals which can be used include molybdenum, tungsten, nickel, cobalt, etc. Where non-noble metals are used it is generally preferred to use a combination of metals, typically at least one Group VIII metal and one Group VIB metal, e.g., nickel-molybdenum, cobalt-molybdenum, nickel-tungsten, and cobalt-tungsten. The non-noble metal hydrogenation metal are usually present in the final catalyst composition as oxides, or more preferably, as sulfides when such compounds are readily formed from the particular metal involved. Preferred non-noble metal overall catalyst compositions contain in excess of about 5 weight percent, preferably about 5 to about 40 weight percent molybdenum and/or tungsten, and at least about 0.5, and generally about 1 to about 15 weight percent of nickel and/or cobalt determined as the corresponding oxides. The sulfide form of these metals is most preferred due to higher activity, selectivity and activity retention.

The hydrogenation components can be incorporated into the overall catalyst composition by any one of numerous procedures. They can be added either to the cracking component or the support or a combination of both. In the alternative, the Group VIII components can be added to the cracking component or matrix component by co-mulling, impregnation, or ion exchange and the Group VI components, i.e.; molybdenum and tungsten can be combined with the refractory oxide by impregnation, co-mulling or co-precipitation. Although these components can be combined with the catalyst support as the sulfides, that is generally not the case. They are usually added as a metal salt which can be thermally converted to the corresponding oxide in an oxidizing atmosphere or reduced to the metal with hydrogen or other reducing agent. The non-nobel metal composition can then be sulfided by reaction with a sulfur donor such as carbon bisulfide, hydrogen sulfide, hydrocarbon thiols, elemental sulfur, and the like.

The cracking component is an acid catalyst material and may be a material such as amorphous silica-alumina or may be a zeolitic or non-zeolitic crystalline molecular sieve. Examples of suitable hydrocracking molecular sieves include zeolite Y, zeolite X and the so called ultra stable zeolite Y and high structural silica:alumina ratio zeolite Y such as for example described in U.S. Pat. Nos. 4,401,556, 4,820,402 and 5,059,567. Small crystal size zeolite Y, such as described in U.S. Pat. No. 5,073,530 can also be used. The disclosures of all of which patents are hereby incorporated by reference in their entirety. Non-zeolitic molecular sieves which can be used include, for example silicoaluminophosphates (SAPO), ferroaluminophosphate, titanium aluminophosphate and the various ELAPO molecular sieves described in U.S. Pat. No. 4,913,799 and the references cited therein. Details regarding the preparation of various non-zeolite molecular sieves can be found in U.S. Pat. No. 5,114,563 (SAPO); U.S. Pat. No. 4,913,799 and the various references cited in U.S. Pat. No. 4,913,799, hereby incorporated by reference in their entirety. Mesoporous molecular sieves can also be included, for example the M41S family of materials (J. Am. Chem. Soc. 1992, 114, 10834–10843), MCM-41 (U.S. Pat. Nos. 5,246, 689, 5,198,203, 5,334,368), and MCM48 (Kresge et al., Nature 359 (1992) 710.)

In general amorphous silica-alumina is more selective for middle distillates, e.g., diesel fuel, whereas crystalline molecular sieves are much more active and produce greater amounts of lighter products, e.g., gasoline. The so-called high (structural) silica-alumina ratio ($Si2O3:Al2O3$=about 50) Y zeolites are less active than the conventional zeolite Y but, are more selective for middle distillate and more active than amorphous silica-alumina. The catalyst also typically contains a matrix or binder material resistant to the conditions used in the hydrocracking reaction. Suitable matrix materials include synthetic or natural substances as well as inorganic materials such as clay, silica and/or metal oxides. The latter may be either naturally occurring or in the form of gelatinous precipitates or gels including mixtures of silica and metal oxides naturally occurring clays which can be composited with the catalyst include those of the montmorillonite and kaolin families. These clays can be used in the raw state as originally mined or initially subjected to calumniation, acid treatment or chemical modification.

The catalyst may be composited with a porous matrix material, such as alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia, and silica-magnesia zirconia. The relative proportions of molecular sieve component and inorganic oxide matrix or binder may vary widely with the molecular sieve content ranging from between 1 to 99, more usually 5 to 80, percent by weight of the composite. The matrix may itself possess catalytic properties generally of an acidic nature, such as for example where amorphous silica-alumina is used as a matrix or binder for a molecular sieve. In general we prefer to use a non-zeolite or low acidic zeolite catalyst, e.g., high structural silica:alumina ratio Y zeolite, as the catalyst where middle distillates is desired as the main commercial product and an acidic zeolite catalyst, e.g., conventional or ultra stabilized Y zeolite, where gasoline is desired as the main commercial product.

Furthermore more than one catalyst type may be used in the reactor. The different catalyst types can be separated into layers or mixed.

The hydrocrackate is then separated into various boiling range fractions. The separation is typically conducted by fractional distillation preceded by one or more vapor-liquid separators to remove hydrogen and/or other tail gases. The fractions separated will typically include a gasoline fraction and a high boiling bottom fraction and one or more intermediate boiling range fractions. The light tail gas fraction, i.e., methane, ethane, proposal and any residual hydrogen is withdrawn and can be for fuel gases or for hydrogen recovery which in turn can be recycled back to the hydrocracker. Typical, liquid/vapor separator systems which can be used to remove tail gases and hydrogen are, for example, described in U.S. Pat. Nos. 3,402,122 and 4,159,937 hereby incorporated by reference in their entirety.

Descriptions of Typical Embodiments

The invention will be further illustrated by following descriptions of typical embodiments. While these particular embodiments are provided to illustrate the present invention, they are not intended to limit it.

Figure 1:
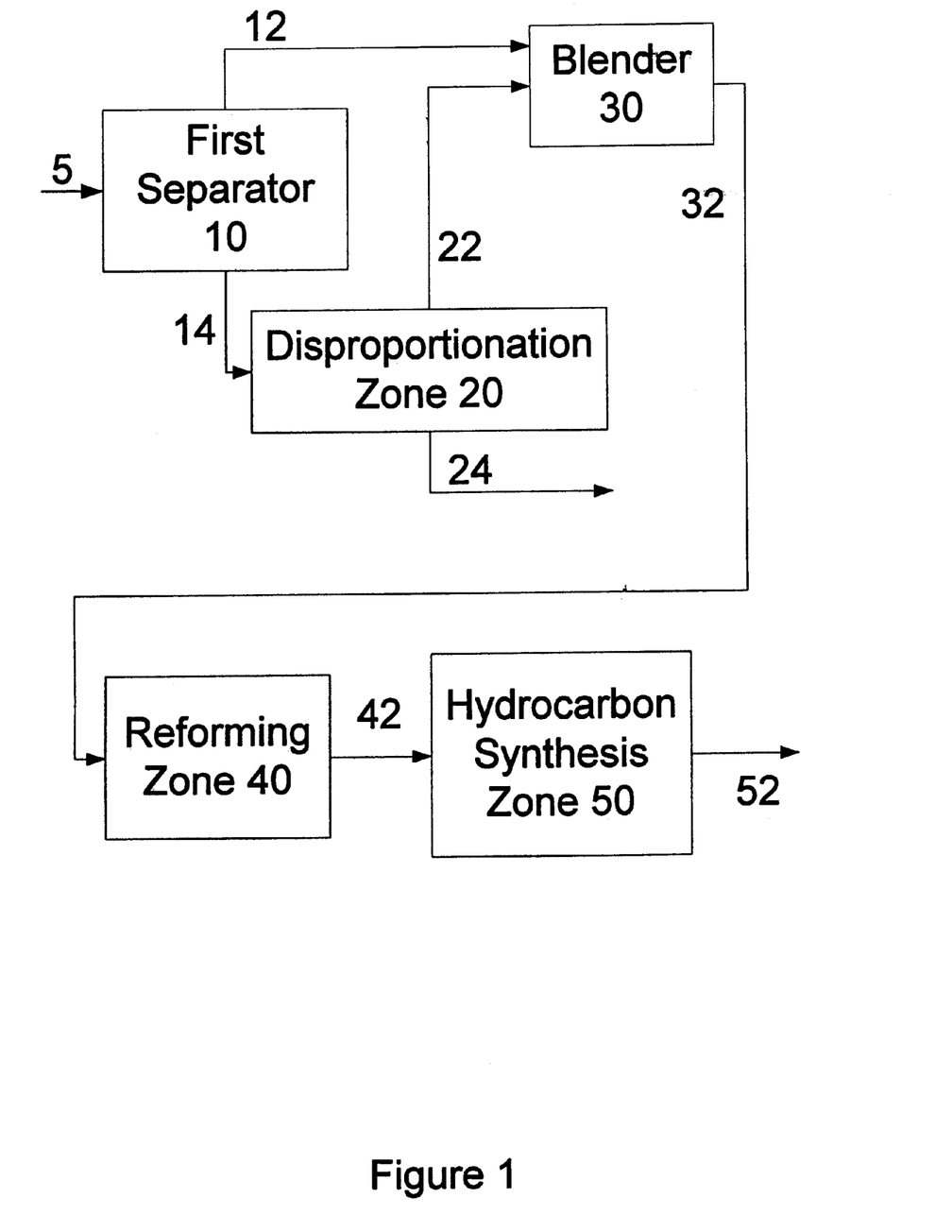
FIG. 1 shows a block diagram of a process for conversion of natural gas and associated light hydrocarbons into methanol, using molecular disproportionation to reduce the amount of gas recycle needed.

FIG. 1 shows a single embodiment for conversion of natural gas and associated light hydrocarbons into methanol, using molecular disproportionation to reduce the amount of gas recycle needed. In that embodiment, a light hydrocarbon gaseous feed 5 comprises alkanes and is free of sulfur, nitrogen, oxygen, and other heteroatoms. This light hydrocarbon gaseous feed 5 is separated in first separator 10 into a lighter fraction 12 comprised of predominately $C_1$ to $C_2$ alkanes and a heavier fraction 14 comprised of predominately $C_3$ and higher alkanes. The heavier fraction 14 is contacted a disproportionation zone 20 with a disproportionation catalyst under conditions selected to convert a significant portion of the alkanes in the heavier fraction by disproportionation into both lower alkanes 22 and higher alkanes 24 (which is a salable product). The lighter fraction 12 and the lower alkanes 22 are blended in blender 30 to form a light hydrocarbon gaseous stream 32 comprised of predominately $C_1$ and $C_2$ alkanes. This light hydrocarbon gaseous stream 32 is reacted with a gaseous oxidant selected from the group consisting of water, carbon dioxide, oxygen, air, or oxygen-enriched air, or mixtures thereof in a reforming zone 40 containing a reforming catalyst under conditions selected to produce a first product stream 42 comprising carbon oxides and hydrogen. The first product stream 42 is contacted in a hydrocarbon synthesis zone (a methanol synthesis zone) 50 with a hydrocarbon synthesis catalyst (a methanol synthesis catalyst) under conditions selected to produce a second product stream 52 comprising salable hydrocarbon products (methanol).

Figure 2:
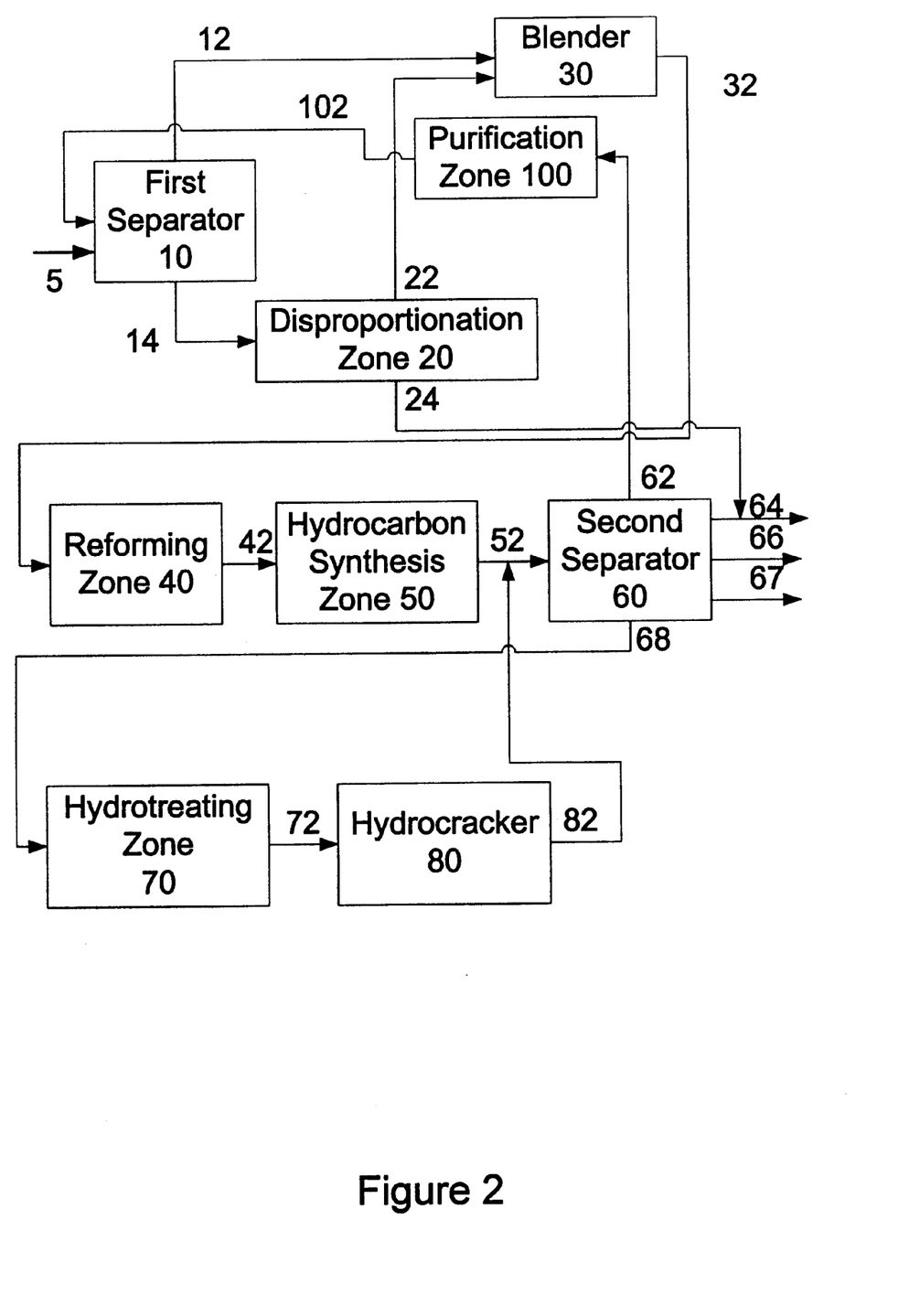
FIG. 2 shows a block diagram of a process for conversion of natural gas and associated light hydrocarbons into naphtha and distillate fuel, using molecular disproportionation to reduce the amount of gas recycle needed.

FIG. 2 shows a single embodiment for conversion of natural gas and associated light hydrocarbons into naphtha, distillate fuel, and hydrocarbons in the lube base oil range using molecular disproportionation to reduce the amount of gas recycle needed. In that embodiment, a light hydrocarbon gaseous feed 5 comprising alkanes and free of sulfur, nitrogen, oxygen, and other heteroatoms is separated in first separator 10 into a lighter fraction 12 comprised of predominately $C_1$ to $C_2$ alkanes and a heavier fraction 14 comprised of predominately $C_3$ and higher alkanes. The heavier fraction 14 is contacted a disproportionation zone 20 with a disproportionation catalyst under conditions selected to convert a significant portion of the alkanes in the heavier fraction by disproportionation into both lower alkanes 22 and higher alkanes 24. The lighter fraction 12 and the lower alkanes 22 are blended in blender 30 to form a light hydrocarbon gaseous stream 32 comprised of predominately $C_1$ and $C_2$ alkanes. This light hydrocarbon gaseous stream 32 is reacted with a gaseous oxidant selected from the group consisting of water, carbon dioxide, oxygen, air, or oxygen-enriched air, or a mixture thereof in a reforming zone 40 containing a reforming catalyst under conditions selected to produce a first product stream 42 comprising carbon oxides and hydrogen. The first product stream 42 is contacted in a hydrocarbon synthesis zone (a Fischer Tropsh zone) 50 with a hydrocarbon synthesis catalyst (a Fischer Tropsh catalyst) under conditions selected to produce a second product stream 52 comprising salable hydrocarbon products (naphtha, distillate fuel, hydrocarbons in the lube base oil range). The second product stream 52 is separated in second separator 60 into a gaseous fraction 62, a naphtha fraction 64, a distillate fuels fraction 66, a hydrocarbons in the lube base oil range fraction 67, and a waxy products fraction 68. The gaseous fraction 62 is passed through a purification zone 100 to remove olefins, sulfur, nitrogen, oxygen, and other heteroatoms to form a purified gaseous fraction 102, which is recycled to first separator 10. The higher alkanes 24 are blended into the naphtha fraction 64. The waxy products fraction 68 is hydrotreated in hydrotreating zone 70 to produce a hydrotreated waxy products fraction 72. This hydrotreated waxy products fraction 72 is hydrocracked in hydrocracker 80 to produce a hydrocracked waxy products fraction 82, which is recycled to the second product stream 52.

Figure 3:
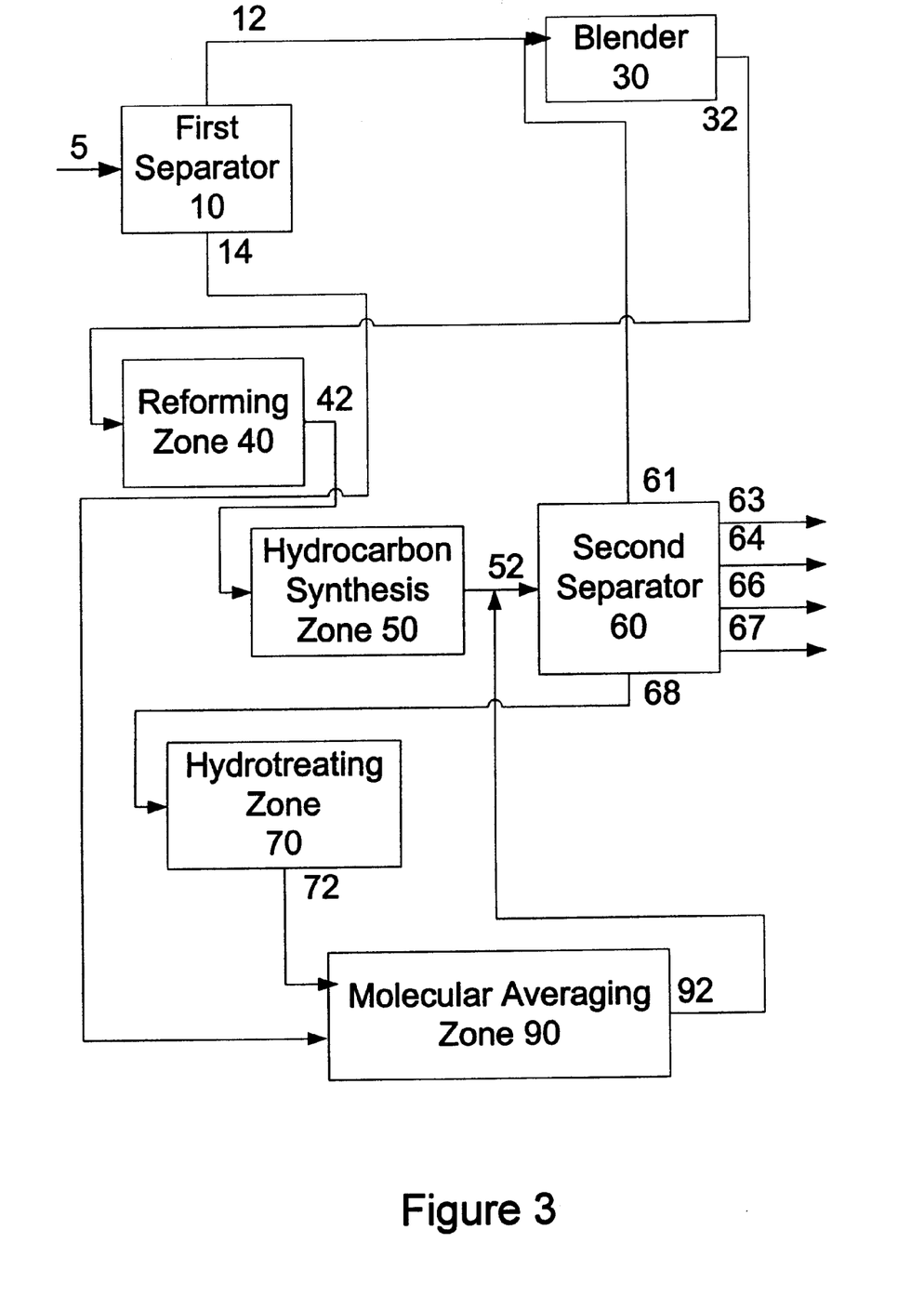
FIG. 3 shows a block diagram of a process for conversion of natural gas and associated light hydrocarbons into naphtha distillate fuel, and hydrocarbons in the lube base oil range, using molecular disproportionation to reduce the amount of gas recycle needed, and to increase the yield of the desired salable product.

FIG. 3 shows a single embodiment for conversion of natural gas and associated light hydrocarbons into naphtha and distillate fuel, using molecular averaging to reduce the amount of gas recycle needed. In that embodiment, a light hydrocarbon gaseous feed 5 comprising alkanes and free of sulfur, nitrogen, oxygen, and other heteroatoms is separated in first separator 10 into a lighter fraction 12 comprised of predominately $C_1$ to $C_2$ alkanes and a heavier fraction 14 comprised of predominately $C_3$ and higher alkanes. That lighter fraction 12 and a gaseous fraction 61 (described below) are blended in blender 30 to form a light hydrocarbon gaseous stream 32. This light hydrocarbon gaseous stream 32 is reacted with a gaseous oxidant selected from the group consisting of water, carbon dioxide, oxygen, air, or oxygen-enriched air, or mixtures thereof in a reforming zone 40 containing a reforming catalyst under conditions selected to produce a first product stream 42 comprising carbon oxides and hydrogen. The first product stream 42 is contacted in a hydrocarbon synthesis zone (a Fischer Tropsh zone) 50 with a hydrocarbon synthesis catalyst (a Fischer Tropsh catalyst) under conditions selected to produce a second product stream 52 comprising salable hydrocarbon products (naphtha and distillate fuel). The second product stream 52 is separated in second separator 60 into a gaseous fraction 61 of predominately $C_{2-}$ alkanes, a gaseous fraction 63 of predominately $C_3$–$C_6$ alkanes, a naphtha fraction 64, a distillate fuels fraction 66, a hydrocarbons in the lube base oil range fraction 67, and a waxy products fraction 68. The gaseous fraction 61 of predominately $C_{2-}$ alkanes is recycled to blender 30. The waxy products fraction 68 is hydrotreated in hydrotreating zone 70 to produce a hydrotreated waxy products fraction 72. The hydrotreated waxy products fraction 72 and the heavier fraction 14 are reacted in a molecular averaging zone 90 with a disproportionation catalyst under conditions selected to convert produce a third product stream 92 comprising salable products. That third product stream 92 is recycled to the second product stream 52.

Referring to FIGS. 2 and 3, although these specific embodiments both show the use of a hydrotreating zone 70, other purification techniques (such as adsorption or extraction) can be used instead of (or in addition to) hydrotreating to remove oxygen and other impurities. Also, although these specific embodiments both show the formation of a naphtha fraction 64, a distillate fuels fraction 66, a hydrocarbons in the lube base oil range fraction 67, and a waxy products fraction 68, other fractions of salable products can be formed instead of (or in addition to) these fractions.

Referring to the specific embodiment shown in FIG. 3, although this specific embodiment shows only the hydrotreated waxy products fraction 72 and the heavier fraction 14 being reacted in a molecular averaging zone 90, other fractions can be sent instead of (or in addition to) either or both of these fractions, as long as these other fractions are treated to remove oxygen and other impurities prior to going to the molecular averaging zone 90. Those possible other fractions include a naphtha fraction, a distillate fuels fraction, a lube feedstock fraction, or any other salable products fraction.

While the present invention has been described with reference to specific embodiments, this application is intended to cover those various changes and substitutions that may be made by those skilled in the art without departing from the spirit and scope of the appended claims.

What is claimed is:

1. In a process for the preparation of salable hydrocarbon products comprising:
   (a) reacting a light hydrocarbon gaseous stream with a gaseous oxidant in at least one reforming zone containing a reforming catalyst under conditions selected to produce a first product stream comprising carbon oxides and hydrogen;
   (b) contacting said first product stream in a hydrocarbon synthesis zone with a hydrocarbon synthesis catalyst under conditions selected to produce a second product stream comprising salable hydrocarbon products; and
   (c) separating said second product stream into at least a gaseous fraction and at least one fraction of salable hydrocarbon products;
   the improvement comprising forming said light hydrocarbon gaseous stream by the process comprising:
   (d) separating a light hydrocarbon gaseous feed comprising alkanes into a lighter fraction and a heavier fraction;
   (e) contacting at least a portion of said heavier fraction of step (d) in a disproportionation zone with a disproportionation catalyst under conditions selected to convert a significant portion of the alkanes in said heavier fraction by disproportionation into both higher alkanes and lower alkanes; and
   (f) forming said light hydrocarbon gaseous stream of step (a) from at least some of said lighter fraction of step (d) and at least some of said lower alkanes of step (e), wherein said light hydrocarbon gaseous stream is comprised of predominately $C_1$ and $C_2$ alkanes.

2. A process for the preparation of salable hydrocarbon products according to claim 1 wherein said gaseous oxidant is selected from the group consisting of water, carbon dioxide, oxygen, air, or oxygen-enriched air, and mixtures thereof.

3. A process for the preparation of salable hydrocarbon products according to claim 1 wherein said hydrocarbon synthesis zone is a methanol synthesis zone and wherein at least one fraction of salable hydrocarbon products comprises methanol.

4. A process for the preparation of salable hydrocarbon products according to claim 1 wherein said hydrocarbon synthesis zone is a Fischer Tropsch zone.

5. A process for the preparation of salable hydrocarbon products according to claim 4 wherein said at least one fraction of salable hydrocarbon products comprises at least a naphtha fraction and a distillate fuels fraction.

6. A process for the preparation of salable hydrocarbon products according to claim 4 wherein, in step (c), said second product stream is separated into at least a gaseous fraction, at least one fraction of salable hydrocarbon products, and a waxy products fraction.

7. A process for the preparation of salable hydrocarbon products according to claim 6 wherein said waxy products fraction is hydrocracked and recycled to the second product stream.

8. A process for the preparation of salable hydrocarbon products according to claim 5 wherein said higher alkanes of step (e) are blended into said salable hydrocarbon products.

9. A process for the preparation of salable hydrocarbon products comprising:
   (a) separating a light hydrocarbon gaseous feed comprising alkanes into a lighter fraction comprised of predominately $C_1$ to $C_2$ alkanes and a heavier fraction comprised of predominately $C_3$ and higher alkanes;
   (b) contacting at least a portion of said heavier fraction of step (a) in a disproportionation zone with a disproportionation catalyst under conditions selected to convert a significant portion of the alkanes in said heavier fraction by disproportionation into both higher and lower alkanes;
   (c) forming a light hydrocarbon gaseous stream comprised of predominately $C_1$ and $C_2$ alkanes from at least some of said lighter fraction of step (a) and at least some of said lower alkanes of step (b);
   (d) reacting said light hydrocarbon gaseous stream with a gaseous oxidant selected from the group consisting of water, carbon dioxide, oxygen, air, or oxygen-enriched air, and mixtures thereof in at least one reforming zone containing a reforming catalyst under conditions selected to produce a first product stream comprising carbon oxides and hydrogen;
   (e) contacting said first product stream in a hydrocarbon synthesis zone with a hydrocarbon synthesis catalyst under conditions selected to produce a second product stream comprising salable hydrocarbon products;
   (f) separating said second product stream into at least a gaseous fraction, a naphtha fraction, a distillate fuels fraction, and a waxy products fraction;
   (g) blending said higher alkanes of step (b) into said naphtha fraction;
   (h) hydrocracking said waxy products fraction; and
   (i) recycling said hydrocracked waxy products fraction to said second product stream.

10. In a process for the preparation of salable hydrocarbon products comprising:
    (a) reacting a light hydrocarbon gaseous stream with a gaseous oxidant in at least one reforming zone containing a reforming catalyst under conditions selected to produce a first product stream comprising carbon oxides and hydrogen;
    (b) contacting said first product stream in a hydrocarbon synthesis zone with a hydrocarbon synthesis catalyst under conditions selected to produce a second product comprising salable hydrocarbon products; and
    (c) separating said second product stream into at least a gaseous fraction of predominately $C_{2-}$ alkanes, a gaseous fraction of predominately $C_3$–$C_6$ alkanes, at least one fraction of salable hydrocarbon products, and a waxy fraction;

the improvement comprising forming said light hydrocarbon gaseous stream by the process comprising:
(d) separating a light hydrocarbon gaseous feed comprising alkanes into a lighter fraction and a heavier fraction;
(e) forming said light hydrocarbon gaseous stream of step (a) from at least some of said lighter fraction of step (d) and at least some of said gaseous fraction of predominately $C_{2-}$ alkanes of step (c), wherein said light hydrocarbon gaseous stream is comprised of predominately $C_1$ and $C_2$ alkanes;
(f) reacting the waxy fraction of step (c) and a lighter process stream in a molecular averaging zone with a disproportionation catalyst under conditions selected to convert a significant portion of said waxy fraction and said lighter process stream by molecular averaging into a third product stream comprising salable products, wherein said lighter process stream is lighter than said waxy fraction and wherein said lighter process stream is selected from the group consisting of said gaseous fraction of predominately $C_3$–$C_6$ alkanes from step (c), at least one fraction of salable hydrocarbon products from step (c), the heavier fraction of step (d), and mixtures thereof.

11. A process for the preparation of salable hydrocarbon products according to claim 10 wherein said gaseous oxidant is selected from the group consisting of water, carbon dioxide, oxygen, air, or oxygen-enriched air, and mixtures thereof.

12. A process for the preparation of salable hydrocarbon products according to claim 10 wherein said at least one fraction of salable hydrocarbon products comprises a naphtha fraction and a distillate fuels fraction.

13. A process for the preparation of salable hydrocarbon products according to claim 10 wherein said lighter process stream of step (f)is the heavier fraction of step (d).

14. A process for the preparation of salable hydrocarbon products according to claim 10 wherein said lighter process stream is isomerized prior to molecular averaging.

15. A process for the preparation of salable hydrocarbon products according to claim 10 wherein said third product stream is recycled to said second product stream.

16. A process for the preparation of salable hydrocarbon products comprising:
(a) reacting a light hydrocarbon gaseous stream with a gaseous oxidant selected from the group consisting of water, carbon dioxide, oxygen, air, or oxygen-enriched air, and mixtures thereof in at least one reforming zone containing a reforming catalyst under conditions selected to produce a first product stream comprising carbon oxides and hydrogen;
(b) contacting said first product stream in a hydrocarbon synthesis zone with a hydrocarbon synthesis catalyst under conditions selected to produce a second product comprising salable hydrocarbon products; and
(c) separating said second product stream into at least a gaseous fraction of predominately $C_{2-}$ alkanes, a gaseous fraction of predominately $C_3$–$C_6$ alkanes, a naphtha fraction, a distillate fuels fraction, and a waxy products fraction;
the improvement comprising forming said light hydrocarbon gaseous stream by the process comprising:
(d) separating a light hydrocarbon gaseous feed comprising alkanes into a lighter fraction comprised of predominately $C_1$ to $C_2$ alkanes and a heavier fraction comprised of predominately $C_3$ and higher alkanes;
(e) forming said light hydrocarbon gaseous stream of step (a) from at least some of said lighter fraction of step (d) and at least some of said gaseous fraction of predominately $C_2$ alkanes of step (c), wherein said light hydrocarbon gaseous stream is comprised of predominately $C_1$ and $C_2$ alkanes;
(f) reacting the waxy fraction of step (c) and the heavier fraction of step (d) in a molecular averaging zone with a disproportionation catalyst under conditions selected to convert a significant portion of the hydrotreated waxy fraction of step (d) and the heavier fraction of step (e) by molecular averaging into a third product stream comprising salable products; and
(h) recycling said third product stream to said second product stream.

* * * * *